(12) United States Patent
Takei et al.

(10) Patent No.: US 8,545,399 B2
(45) Date of Patent: Oct. 1, 2013

(54) MEDICAL INSTRUMENT

(71) Applicant: Olympus Medical Systems Corp., Tokyo (JP)

(72) Inventors: Shunji Takei, Hachioji (JP); Waturo Ono, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/715,138

(22) Filed: Dec. 14, 2012

(65) Prior Publication Data
US 2013/0150713 A1 Jun. 13, 2013

Related U.S. Application Data

(63) Continuation of application No. PCT/JP2012/062493, filed on May 16, 2012.

(30) Foreign Application Priority Data

Jun. 14, 2011 (JP) ................................. 2011-132588

(51) Int. Cl.
*A61B 1/06* (2006.01)
(52) U.S. Cl.
USPC ............ 600/160; 600/109; 600/407; 600/477
(58) Field of Classification Search
USPC .................. 600/109, 160, 407, 477
See application file for complete search history.

(56) References Cited

U.S. PATENT DOCUMENTS

| | | |
|---|---|---|
| 2006/0170802 A1 | 8/2006 | Misawa |
| 2007/0242145 A1 | 10/2007 | Hazelwood et al. |
| 2008/0180547 A1 | 7/2008 | Hirose |

FOREIGN PATENT DOCUMENTS

| | | |
|---|---|---|
| EP | 2 448 253 A1 | 5/2012 |
| JP | 2002-085342 | 3/2002 |
| JP | 2006-238410 | 9/2006 |
| JP | 2006-319414 | 11/2006 |
| JP | 2009-095538 | 5/2009 |
| JP | 2011-004370 | 1/2011 |
| WO | WO 2010/150638 A1 | 12/2010 |

OTHER PUBLICATIONS

International Search Report dated Aug. 21, 2012 issued in PCT/JP2012/062493.
European Search Report dated Jul. 24, 2013 from corresponding European Application No. 12 80 0917.2.

*Primary Examiner* — Unsu Jung
*Assistant Examiner* — Joel Lamprecht
(74) *Attorney, Agent, or Firm* — Scully, Scott, Murphy & Presser, P.C.

(57) ABSTRACT

A medical instrument is provided with: an illumination section radiating excitation light for exciting a fluorescent substance given to a subject, to the subject; an image pickup section photoelectrically converting reflected light from the subject to which the excitation light is radiated, to pick up an image of the subject; a reading section holding pixel signals obtained by the photoelectrical conversion and capable of reading the pixel signals non-destructively while changing amplification factors of the held pixel signals by a predetermined unit of pixels; and an image processing section determining an arithmetic mean of the pixel signals read with different amplification factors by the reading section to generate an image. The medical instrument improves visibility of each fluorescent area without occurrence of position displacement even in the case where multiple fluorescent areas with a relatively large brightness/darkness difference exist within one screen.

9 Claims, 6 Drawing Sheets

(a)    (b)

(a)    (b)

(c)

MEDICAL INSTRUMENT

CROSS REFERENCE TO RELATED APPLICATION

This application is a continuation application of PCT/JP2012/062493 filed on May 16, 2012 and claims benefit of Japanese Application No. 2011-132588 filed in Japan on Jun. 14, 2011, the entire contents of which are incorporated herein by this reference.

BACKGROUND OF THE INVENTION

1. Field of the Invention

The present invention relates to a medical instrument preferable for fluorescence observation.

2. Description of the Related Art

Recently, attention has been focused on a cancer diagnosis technique using a molecular target drug. The technique is such that, after spraying or injecting a fluorescence probe (fluorescence medicine) targeting a biological protein which specifically appears in a cancer cell on or into a target site of a living body, it is determined whether cancer exists or not on the basis of fluorescence emitted at the target site. The technique is useful for an early detection of cancer in a field of digestive tracts.

Diagnosis using the technique is possible in an endoscope apparatus. That is, by radiating excitation light from a light source apparatus to an object and catching fluorescence from fluorescence medicine accumulated in cancer, diagnosis of existence of cancer or qualitative diagnosis, such as diagnosis of degree of malignancy, is performed. Note that Japanese Patent Application Laid-Open Publication No. 2009-95538 discloses an electronic endoscope capable of generally performing both of normal white color light observation and fluorescence observation.

SUMMARY OF THE INVENTION

A medical instrument according to one aspect of the present invention is provided with: an illumination section radiating excitation light for exciting a fluorescent substance given to a subject, to the subject; an image pickup section photoelectrically converting reflected light from the subject to which the excitation light is radiated, to pick up an image of the subject; a reading section holding pixel signals obtained by the photoelectrical conversion and capable of reading the pixel signals non-destructively while changing amplification factors of the held pixel signals by a predetermined unit of pixels; and an image processing section determining an arithmetic mean of the pixel signals read with different amplification factors by the reading section to generate an image.

DETAILED DESCRIPTION OF THE PREFERRED EMBODIMENT

An embodiment of the present invention will be described below in detail with reference to drawings.

Figure 1:
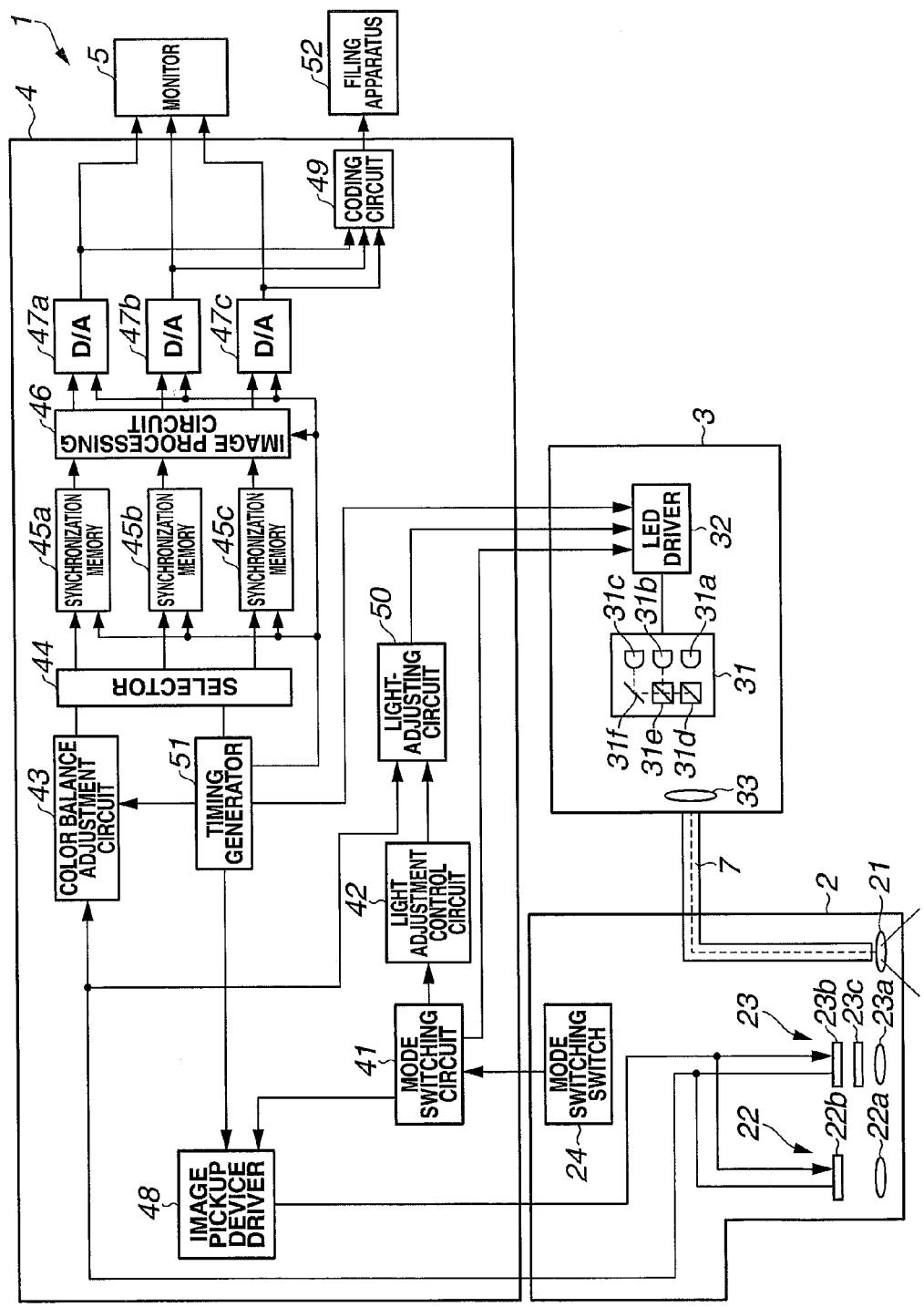
FIG. 1 is a block diagram showing a medical instrument according to an embodiment of the present invention.

FIG. 1 is a block diagram showing a medical instrument according to an embodiment of the present invention.

Figure 2:
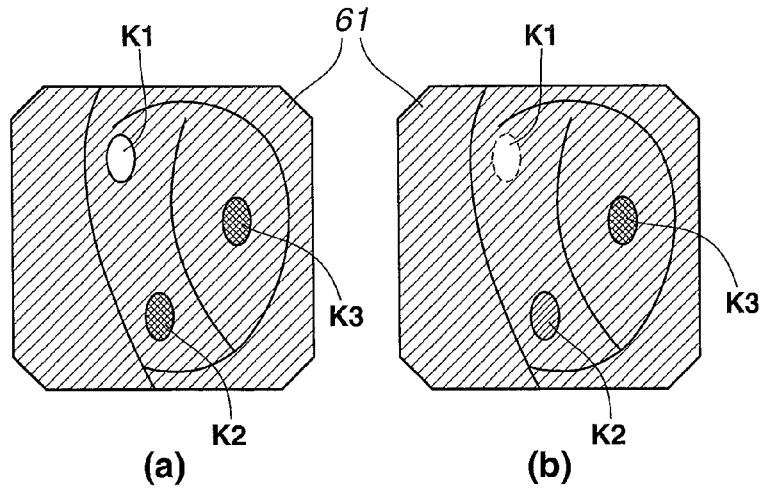
FIG. 2 is a diagram showing an endoscopic image 61 in which multiple fluorescent areas K1 to K3 exist in one screen.

First, a technique of the present embodiment for improving visibility of a fluorescent area will be described with reference to FIGS. 2 to 7. FIG. 2 is a diagram showing an endoscopic image 61 in which multiple fluorescent areas K1 to K3 exist in one screen. FIGS. 2(a) and 2(b) are obtained by performing image pickup of the same object by performing different light adjustment controls. In FIG. 2, as for fluorescent areas K1 to K3, it is shown that the finer the hatching is, the darker the area is, and non-hatching indicates a bright area.

FIG. 2(a) shows an image obtained by performing image pickup by performing light adjustment control on the basis of the bright fluorescent area K1, and FIG. 2(b) shows an image obtained by performing image pickup by performing light adjustment control on the basis of the dark fluorescent area K3. In the case of FIG. 2(a), it is shown that the dark fluorescent areas K2 and K3 have been image-picked up extremely dark, and visibility is considerably low. In the case of FIG. 2(b), it is shown by a broken line that the bright fluorescent area K1 has been image-picked up in a saturated state, and halation has occurred.

Figure 3:
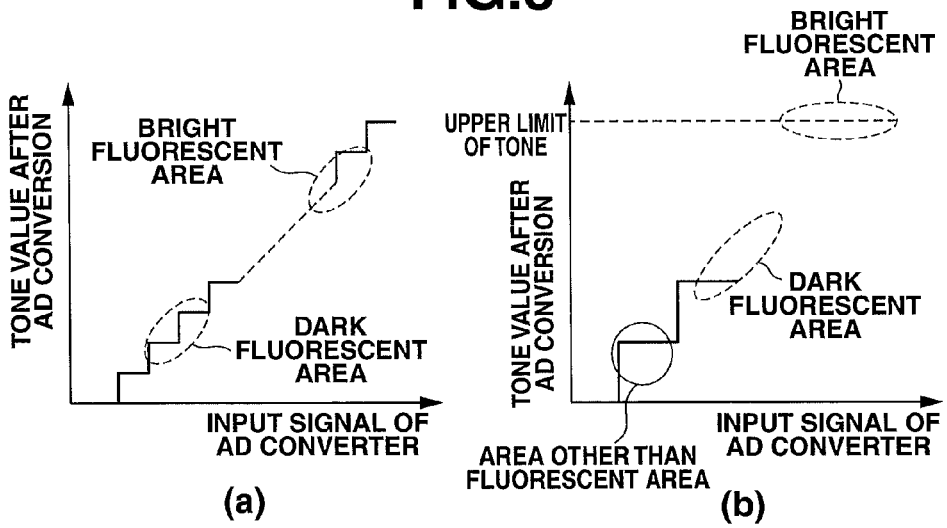
FIG. 3 is a diagram for illustrating a conventional example of processing.

Thus, as described above, a method is thought of in which, by generating two images with different amplification factors changed by digital processing, from one image obtained from an endoscope, and determining an arithmetic mean of the images, brightness is corrected while a problem of position displacement is solved. FIG. 3 is a diagram for illustrating the processing. FIGS. 3(a) and 3(b) show level change in the case of amplifying an output of an ADC (analog-digital converter), with an input signal and an output signal indicated by a horizontal axis and a vertical axis, respectively. FIG. 3(a) shows an example of an amplification factor for ADC output being relatively low, and FIG. 3(b) shows an example of the amplification factor for ADC output being relatively high.

FIG. 3(a) shows that the amplification factor is low, and a bright fluorescent area is amplified to be sufficiently bright while a dark fluorescent area remains relatively dark and lacks visibility. On the other hand, when the amplification factor of A/D conversion output is set higher, as shown in FIG. 3(b), the bright fluorescent area is saturated, and the dark fluorescent area is sufficiently bright.

Fluorescence medicine specifically accumulates on a cancer. Therefore, the medicine accumulates at a high concentration mainly on a cancer lesion and the lesion becomes a fluorescent area, and a part other than the lesion, which is not a fluorescent area, becomes of a sufficiently dark black level because the medicine hardly accumulates there. On the other hand, if brightness/darkness difference is large between a bright fluorescent area and a dark fluorescent area due to the kind of fluorescence medicine or difference in observation distance, it is necessary to perform amplification at an extremely high amplification factor in order to improve visibility of the dark fluorescent area. When the brightness/darkness difference is small between a black part other than fluorescent areas and a dark fluorescent area part, however, the state is a state that difference between levels of A/D-converted digital signals is small. Therefore, if the digital signals are amplified at an extremely high amplification factor in that state, the level of the black part other than fluorescent areas is also high similarly to the dark fluorescent area, and the whole image becomes whitish.

That is, in the case where the amplification factor is relatively high as in FIG. 3(b), in comparison with FIG. 3(a), the dynamic range is narrow, and not only the level of the dark fluorescent area but also the black level of the area other than fluorescent areas is high, and the whole becomes whitish.

Figure 4:
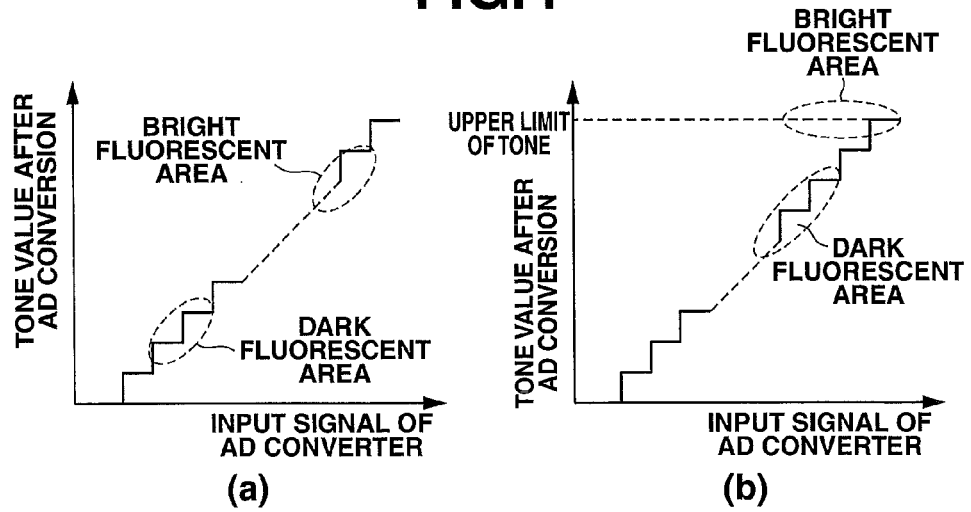
FIG. 4 is a diagram for illustrating a tone value of an ADC output.

Accordingly, in the present embodiment, by performing amplification in an analog state before A/D conversion, level difference between signals of a part other than fluorescent areas after A/D conversion and a dark fluorescent area part is appropriately maintained so that original brightness difference can be expressed. FIG. 4 is a diagram for illustrating a tone value of an ADC output in this case. FIGS. 4(a) and 4(b) show level change in the case of performing amplification at a pre-stage of the ADC, with an input signal and an output signal indicated by a horizontal axis and a vertical axis, respectively. FIG. 4(a) shows an example of an amplification factor at the pre-stage of the ADC being relatively low, and FIG. 4(b) shows an example of the amplification factor at the pre-stage of the ADC being relatively high.

In both of the cases of FIGS. 4(a) and 4(b), the dynamic range of an output relative to an ADC input does not change. In FIG. 4(b), the level of a dark fluorescent area is sufficiently high, while the level of a black level part of an area other than fluorescent areas remains low. It does not happen that the whole becomes whitish.

Figure 5:
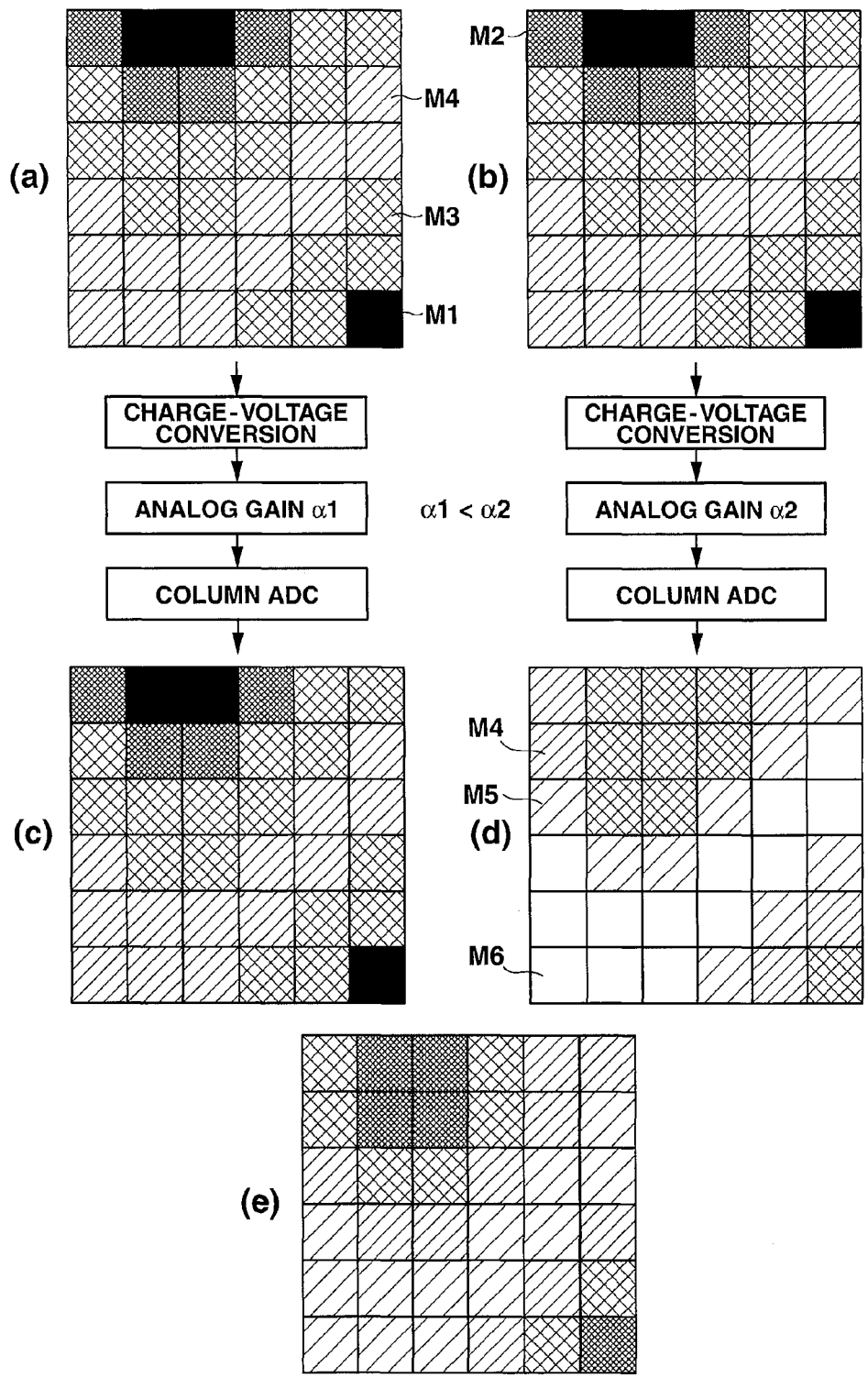
FIG. 5 is a diagram for illustrating a process in the present embodiment.

FIG. 5 is a diagram for illustrating a process in the present embodiment.

In the present embodiment, a CMOS sensor is used as an image pickup device to pick up a fluorescence image from an object, as described later. Reading from the CMOS sensor is performed twice non-destructively. FIGS. 5(a) and 5(b) show optical images obtained by the CMOS sensor receiving light from an object. Description will be made on the assumption that the CMOS sensor is configured with vertical and horizontal 6×6 pixels, to simplify the description.

In FIG. 5, brightness of pixels is indicated by fineness and roughness of hatching. A filled pixel M1 is the darkest pixel, and a white pixel M6 is the brightest pixel. An example is shown in which six kinds of pixels M1 to M6 exist, the pixels M1 to M6 being in darkness order with M1 as the darkest.

The CMOS sensor photoelectrically converts a received optical image to output an image signal. At the first reading, the optical image in FIG. 5(a) is amplified by analog gain $\alpha 1$ after being photoelectrically converted, and then, converted to a digital signal and outputted by a column ADC. Note that the gain $\alpha 1$ is set, for example, to such a value that a bright pixel area is not saturated. FIG. 5(c) shows an image obtained in this way. Note that the column ADC is adapted to perform output after adjusting an output level after digital conversion.

Next to the first reading, the second reading is performed. It is generally necessary to receive light again to re-accumulate a signal each time reading is performed once. However, since the first and second readings are performed by non-destructive reading by the CMOS sensor, the optical image obtained by the CMOS sensor receiving light at the time of the first reading is held until the second reading. At the second reading also, the same optical image as the first time (FIG. 5(b)) is used.

In the present embodiment, the image signal obtained by the CMOS sensor photoelectrically converting the optical image in FIG. 5(b) is converted to a digital signal by the column ADC after being amplified by analog gain $\alpha 2$, at the second reading, and is outputted. The gain $\alpha 2$ is set so that a dark pixel area is optimally bright. FIG. 5(d) shows an image obtained in this way. As apparent from comparison between FIGS. 5(b) and 5(d), $\alpha 1 < \alpha 2$ is satisfied. Since amplification by the relatively high gain $\alpha 2$ is performed at the time of the second reading, the image shown in FIG. 5(d) is configured with pixels M6, M5 and M4 which are relatively brighter than the image in FIG. 5(c).

In the present embodiment, an arithmetic mean of the images shown in FIGS. 5(c) and 5(d) is determined. FIG. 5(e) shows an image determined in this way. As shown in FIG. 5(e), the image obtained by determining the arithmetic mean of FIGS. 5(c) and 5(d) is such that dark pixel areas are relatively bright pixels M2, and the visibility is good. Furthermore, bright pixel areas are pixels M5, which are not too bright, and saturation can be avoided.

Figure 6:
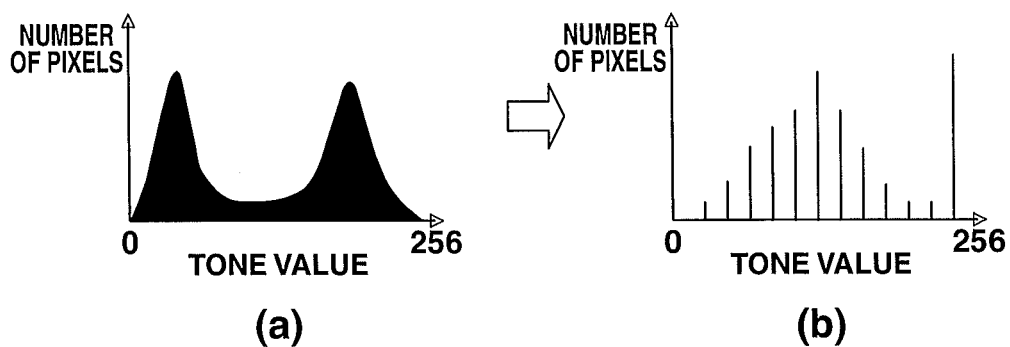
FIG. 6 is a diagram for illustrating an advantage according to the present embodiment.
Figure 7:
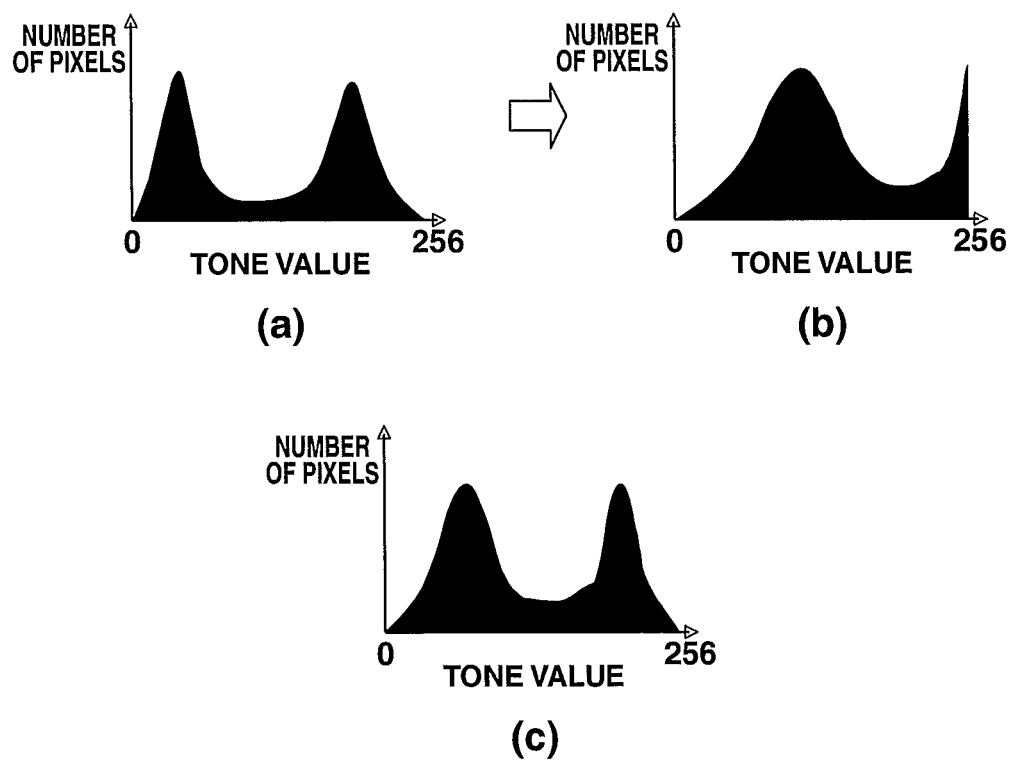
FIG. 7 is a diagram for illustrating an advantage according to the present embodiment.

FIGS. 6 and 7 are diagrams for illustrating advantages according to the present embodiment. FIGS. 6(a) and 6(b) and FIGS. 7(a) to 7(c) show histograms illustrating influence of amplification before and after A/D conversion, with a tone value and the number of pixels indicated by a horizontal axis and a vertical axis, respectively. FIGS. 6(a) and 7(a) show picked-up images obtained by photoelectrical conversion by an image pickup device. Tone change (gradation) of the picked-up images of FIGS. 6(a) and 7(a) are smooth.

FIG. 6(b) shows a histogram in the case of amplifying a picked-up image after A/D-converting the image. As shown in FIG. 6(b), the picked-up image of FIG. 6(a) is amplified by multiplication by excessive gain for a dark area. However, some tones are omitted. Therefore, smooth gradation is not obtained. Consequently, even if an arithmetic mean of the images of FIGS. 6(a) and 6(b) is determined, an appropriate image is not obtained.

On the other hand, FIG. 7(b) is such that a picked-up image is amplified before A/D conversion, as described with reference to FIG. 5, and change in the envelope is the same as FIG. 6(b), but omission of some tones does not occur. Consequently, smooth gradation is obtained. When an arithmetic mean of the images of FIGS. 7(a) and 7(b) is determined, an image of FIG. 7(c) is obtained. In the image of FIG. 7(c), tone change is appropriately maintained, and a dark area becomes brighter while saturation of brightness in a bright area is prevented. That is, it is possible to correct brightness/darkness difference between the dark area and the bright area and obtain an image easy to recognize.

(Circuit Configuration)

In FIG. 1, an endoscope 2 is configured to have an illumination optical system 21 that emits light supplied from a light source device 3 and transmitted by a light guide 7 to an object, an image pickup section for white color light observation 22, an image pickup section for fluorescence observation 23, and a mode switching switch 24 with which an operation for switching the observation mode of an endoscope apparatus 1 can be performed.

The image pickup section for white color light observation 22 is configured to have an objective optical system 22a that forms an image of an object, a CMOS sensor 22b in which an image pickup surface provided with a primary color filter is arranged to correspond to the image forming position of the objective optical system 22a.

The CMOS sensor 22b is drive-controlled by an image pickup device driver 48 in a processor 4, and the CMOS sensor 22b generates an image pickup signal by performing photoelectrical conversion of return light from an object the image of which is formed on the image pickup surface, and outputs the signal to the processor 4.

The image pickup section for fluorescence observation 23 is configured to have an objective optical system 23a that forms an image of an object, a monochrome CMOS sensor 23b the image pickup surface of which is arranged to correspond to the image forming position of the objective optical system 23a, and an excitation light cut filter 23c arranged at a pre-stage of the CMOS sensor 23b.

The CMOS sensor 23b is drive-controlled by the image pickup device driver 48 in the processor 4, and the CMOS sensor 23b generates an image pickup signal by performing photoelectrical conversion of return light from an object the image of which is formed on the image pickup surface and outputs the signal to the processor 4. The CMOS sensor 23b has an amplification function for each pixel and is configured such that the amplification factor can be controlled by the image pickup device driver 48.

Figure 8:
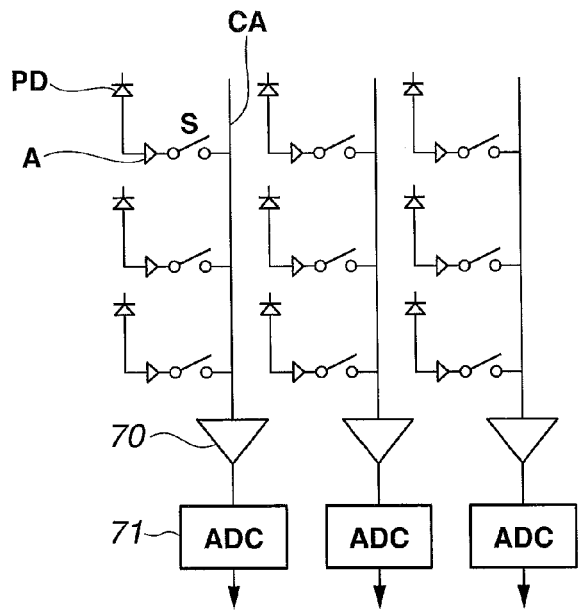
FIG. 8 is a schematic circuit diagram showing a configuration of a CMOS sensor 23b.

FIG. 8 is a schematic circuit diagram showing a configuration of the CMOS sensor 23b. In the CMOS sensor 23b, pixels are arranged in a matrix, and each pixel is configured with a photodiode PD, an amplification section A and a switch S. The photodiode PD generates charge according to received light. After being amplified by the amplification section A, voltage change due to the charge generated in the photodiode PD is outputted to a column line CA via the switch S. The amplification factor of the amplification section A can be controlled by the image pickup device driver 48.

All switches S on one column are connected to a common column line CA. By switches S on the same line being on at the same time, signals are provided from all pixels on the same line to the respective CDS circuits 70 via the respective column lines CA. By switches S being selectively turned on for each line by a vertical scanning circuit not shown, signals (pixel signals) of all pixels are outputted via the column lines CA.

Each CDS circuit 70 removes reset noise from the signal inputted via each column line CA and, after that, outputs each signal to each ADC 71. Each ADC 71 converts the inputted signal to a digital signal and, after that, outputs the signal. Outputs from the respective ADC 71 are sequentially outputted by a horizontal scanning circuit not shown.

The excitation light cut filter 23c is formed being provided with such an optical characteristic that blocks the wavelength band of excitation light emitted from an excitation light LED 31b to be described later and causes each of the wavelength band of fluorescence emitted from a fluorescent substance, such as fluorescence medicine, excited by the excitation light and the wavelength band of reference light emitted from a reference light LED 31c to be described later to be transmitted.

The light source device 3 has an LED light source section 31, an LED driver 32, and a condensing optical system 33 that condenses light emitted by the LED light source section 31 and supplies the light to the light guide 7. The LED light source section 31 is configured to have a white color light LED 31a, the excitation light LED 31b, the reference light LED 31c, a half mirror 31d, a half mirror 31e and a mirror 31f. The white color light LED 31a is configured so as to be able to emit white color light (for example, visible light of 400 to 690 nm) that includes each of the wavelength bands of R (red), G (green) and B (blue).

The excitation light LED 31b is configured so as to be able to emit excitation light (for example, near infrared light of 700 nm) with a wavelength band capable of exciting a fluorescent substance such as fluorescence medicine. The reference light LED 31c is configured so as to be able to emit reference light (for example, near infrared light of 800 nm) with a wavelength band that overlaps neither the wavelength band of excitation light emitted from the excitation light LED 31b nor the wavelength band of fluorescence emitted from a fluorescent substance, such as fluorescence medicine, excited by the excitation light.

The half mirror 31d is arranged on an optical path between the white color light LED 31a and the condensing optical system 33, and configured being provided with such an optical characteristic that causes white color light emitted from the white color light LED 31a to be transmitted to the condensing optical system 33 side and reflects excitation light and reference light emitted via the half mirror 31e to the condensing optical system 33 side.

The half mirror 31e is arranged on an optical path between the half mirror 31d and the mirror 31f, and is configured being provided with such an optical characteristic that reflects excitation light emitted from the excitation light LED 31b to the half mirror 31d side and causes reference light emitted via the mirror 31f to be transmitted to the half mirror 31d side. The mirror 31f is configured being provided with such an optical characteristic that reflects reference light emitted from the reference light LED 31c to the half mirror 31e side.

The LED driver 32 is configured so as to be able to supply a drive current for driving each LED provided in the LED light source section 31. Therefore, for example, as the size of the drive current supplied from the LED driver 32 to the LED light source section 31 changes, the strength of light (white color light, excitation light and reference light) emitted from the LED light source section 31 changes.

On the other hand, the LED driver 32 operates so as to cause each LED provided in the LED light source section 31 to emit light or stop light emission according to control by the processor 4. That is, the LED driver 32 controls the LED light source section 31 according to the observation mode. The observation mode can be set by the mode switching switch 24. The mode switching switch 24 outputs an operation signal corresponding to a surgeon's operation, to a mode switching circuit 41.

The mode switching circuit 41 generates a mode switching control signal for causing each section of the endoscope apparatus 1 to perform an operation corresponding to an observation mode selected by an operation of the mode switching switch 24, and outputs the signal to a light adjustment control circuit 42, the LED drive 32 and the image pickup device driver 48.

The light adjustment control circuit 42 is adapted to set a brightness target value and the like corresponding to an observation mode, for a light-adjusting circuit 50. The brightness target value corresponding to an observation mode is set for the light-adjusting circuit 50 by the light adjustment control circuit 42, and the light-adjusting circuit 50 generates a light adjustment signal for adjusting brightness of an image pickup signal on the basis of the set target value and the level of the image pickup signal and outputs the signal to the LED driver 32.

The LED driver 32 is also given a timing signal from a timing generator 51. The timing generator 51 generates and outputs a timing signal for causing operations of the respective sections of the processor 4 to be appropriately synchronized. For example, when the endoscope apparatus 1 is switched to a fluorescence observation mode, the timing generator 51 generates and outputs a timing signal for causing each section of the processor 4 to perform an operation synchronized with a period during which the excitation light LED 31b emits light (or stops light emission) and a period during which the reference light LED 31c emits light (or stops light emission).

When detecting that the endoscope apparatus 1 has been switched to the white color light observation mode, on the basis of a mode switching control signal outputted from the mode switching circuit 41 of the processor 4, the LED driver 32 operates so as to cause the white color light LED 31a to emit light and cause the excitation light LED 31b and the reference light LED 31c to stop light emission. When detecting that the endoscope apparatus 1 has been switched to the fluorescence observation mode, on the basis of a mode switching control signal outputted from the mode switching circuit 41, the LED driver 32 operates so as to cause the white color light LED 31a to stop light emission and cause the excitation light LED 31b and the reference light LED 31c to alternately emit light. Note that the LED driver 32 may cause only excitation light to be emitted in the fluorescence observation mode.

The processor 4 has a color balance adjustment circuit 43 that performs color balance adjustment processing, a multiplexer 44 that performs an operation related to sorting of signals, synchronization memories 45a, 45b and 45c, an image processing circuit 46 that performs predetermined image processing, and DACs 47a, 47b and 47c that perform D/A conversion processing.

Both of an image pickup signal outputted from the CMOS sensor 22b in the white color light observation mode and a digital image pickup signal outputted from the CMOS sensor 23b in the fluorescence observation mode are inputted to the processor 4. The color balance adjustment circuit 43 performs color balance adjustment processing of a digital image pickup signal on the basis of a timing signal from the timing generator 51 and outputs the signal to the selector 44.

The selector 44 separates the image pickup signal outputted from the color balance adjustment circuit 43 on the basis of a timing signal from the timing generator 51 into signals of three channels according to the mode and outputs the respective separated signals, allocating the signals to the synchronization memories 45a, 45b and 45c. Each of the synchronization memories 45a, 45b and 45c has a configuration capable of temporarily storing each signal outputted from the selector 44. For example, at the time of white color light observation mode, signals of respective color components separated from an image pickup signal are stored in the synchronization memories 45a, 45 and 45c, respectively. At the time of the fluorescence observation mode, a signal based on the first reading, a signal based on the second reading and a signal based on a picked-up image obtained by exposure of reference light are stored in the synchronization memories 45a, 45 and 45c, respectively, as described later.

The image processing circuit 46 reads the signals of the respective channels stored in the synchronization memories 45a, 45b and 45c at the same time on the basis of a timing signal from the timing generator 51 and, after that, performs image processing, such as gamma correction, for each of the read signals. Then, the image processing circuit 46 assigns the respective signals which have received image processing, such as gamma correction, to a first color channel (for example, an R component), a second color channel (for example, a G component) and a third color channel (for example, a B component), respectively, to output the signals to the DACs 47a, 47b and 47c.

The signals of the first to third color channels outputted from the image processing circuit 46 are converted to analog signals at the DACs 47a, 47b and 47c, respectively, and outputted to a monitor 5. Thereby, an observed image corresponding to each observation mode is displayed on the monitor 5.

Note that outputs of the DACs 47a, 47b and 47c are also given to a coding circuit 49. The coding circuit 49 performs coding processing of the inputted signals and outputs them to a filing apparatus 52. The filing apparatus 52 performs filing of the coded data which have been inputted.

The image pickup device driver 48 is provided with a timing signal from the timing generator 51 and drives the CMOS sensor 22b and the CMOS sensor 23b. For example, when detecting that the endoscope apparatus 1 has been switched to the white color light observation mode, on the basis of a mode switching control signal of the mode switching circuit 41, the image pickup device driver 48 drives the CMOS sensor 22b and stops driving of the CMOS sensor 23b. Furthermore, when detecting that the endoscope apparatus 1 has been switched to the fluorescence observation mode, on the basis of a mode switching control signal, the image pickup device driver 48 drives the CMOS sensor 23b and stops driving of the CMOS sensor 22b.

In the present embodiment, the image pickup device driver 48 controls the CMOS sensor 23b to perform reading non-destructively twice during one exposure period in the fluorescence observation mode. The image pickup device driver 48 resets charge accumulated in the photodiode PD of each pixel each time the two-time readings end. Then, at the time of one reading of the two-time readings, gain of the amplification section A of each pixel is set to $\alpha 1$. At the time of the other reading, the gain of the amplification section A of each pixel is set to $\alpha 2$. Note that $\alpha 1 < \alpha 2$ is satisfied. For example, the image pickup device driver 48 sets the gain $\alpha 1$ to a value at such a level that a bright pixel area is not saturated and sets the gain $\alpha 2$ so that a dark pixel area is optimally bright.

In the case of radiating excitation light and reference light alternately in the fluorescence observation mode, reading is performed non-destructively twice during one fluorescence exposure period based on radiation of excitation light, and reading is performed once during one reference light exposure period based on radiation of reference light. The gain at the time of performing two-time readings during the fluorescence exposure period is switched between $\alpha 1$ and $\alpha 2$ and the gain of the amplification section A during the reference light exposure period is set to $\beta$. Note that $\beta < \alpha 1 < \alpha 2$ is satisfied.

Note that, in the fluorescence observation mode, a signal based on an image pickup signal by the first reading, of image pickup signals by the non-destructive two-time readings, is stored in the synchronization memory 45a and an image pickup signal by the second reading is stored in the synchronization memory 45b. An image pickup signal based on reference light is stored in the synchronization memory 45c.

Figure 9:
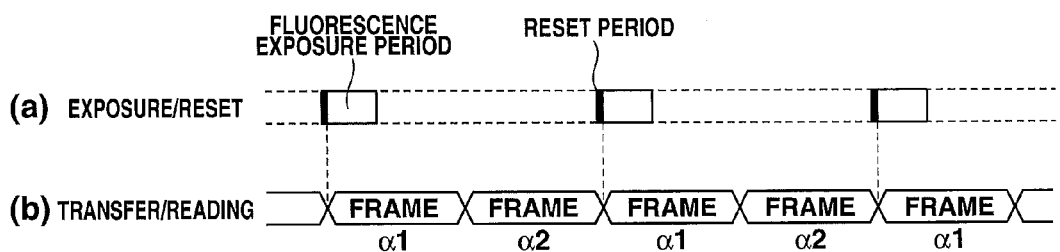
FIG. 9 is a timing chart for illustrating an operation of the present embodiment.

Next, an operation of the embodiment configured as described above will be described with reference to a timing chart in FIG. 9. FIG. 9(a) shows exposure and reset periods, and FIG. 9(b) shows transfer and reading of an image pickup signal.

The surgeon specifies the white color light observation mode or the fluorescence observation mode by operating the mode switching switch 24. The mode switching circuit 41 generates a mode switching control signal based on an operation of the mode switching switch 24 and outputs the generated mode switching control signal to the light adjustment control circuit 42, the LED driver 32 and the image pickup device driver 48.

For example, it is assumed that the white color light observation mode is now specified by the surgeon. In this case, the LED driver 32 causes the white color light LED 31a to emit light and causes the excitation light LED 31b and the reference light LED 31c to stop light emission, on the basis of a mode switching control signal. The image pickup device driver 48 drives the CMOS sensor 22b and stops driving of the CMOS sensor 23b, on the basis of the mode switching control signal.

Thereby, white color light supplied from the light source device 3 is emitted to an object via the light guide 7 and the illumination optical system 21, and return light (reflected light) of the white color light forms an image on the image pickup surface of the CMOS sensor 22b. Then, an image pickup signal obtained by performing image pickup of the return light (reflected light) of the white color light is outputted from the CMOS sensor 22b.

The image pickup signal outputted from the CMOS sensor 22b is inputted to the light-adjusting circuit 50. The light-adjusting circuit 50 generates a light adjustment signal for adjusting the brightness of the image pickup signal to a brightness target value in the white color light observation mode and outputs the light adjustment signal to the LED driver 32, on the basis of the mode switching control signal. The LED driver 32 causes the brightness of the image pickup signal to correspond to the target value by changing a driving current to be supplied to the white color light LED 31a on the basis of the light adjustment signal.

On the other hand, the image pickup signal outputted from the CMOS sensor 22b is outputted to the monitor 5 as a video signal after passing through each of the sections of the color balance adjustment circuit 43, the selector 44, the synchronization memories 45a to 45c, the image processing circuit 46 and the DACs 47a to 47c. In this way, an observed image (a color image) corresponding to the white color light observation mode is displayed on the monitor 5.

It is assumed that the surgeon performs fluorescence observation of a subject next. Before observing a desired observation site inside the subject, the surgeon gives fluorescence medicine to be accumulated in lesion tissue of the desired observation site, to the subject. After that, the surgeon positions the distal end portion of the endoscope 2 near the desired observation site in the subject by performing an operation of inserting the endoscope 2, seeing an observed image displayed on the monitor 5. Then, in such a state, the surgeon selects the fluorescence observation mode by operating the mode switching switch 24.

When detecting that the fluorescence observation mode has been selected by the operation of the mode switching switch 24, the mode switching circuit 41 generates a mode switching control signal corresponding to the fluorescence observation mode and outputs the signal to the light adjustment control circuit 42, the LED driver 32 and the image pickup device driver 48.

On the basis of the mode switching control signal, the LED driver 32 causes the white color light LED 31a to stop light emission, and causes the excitation light LED 31b to emit light or causes the excitation light LED 31b and the reference light LED 31c to alternately emit light. Note that the LED driver 32 controls periods during which the excitation light LED 31b is caused to emit light and stop light emission and periods during which the reference light LED 31c is caused to emit light and stop light emission, on the basis of a timing signal from the timing generator 51. The image pickup device driver 48 drives the CMOS sensor 23b and stops driving of the CMOS sensor 22b, on the basis of the mode switching control signal.

In the present embodiment, the LED driver 32 and the image pickup device driver 48 are adapted to control radiation of excitation light and reading of an image pickup signal so that reading from the CMOS sensor 23b is performed twice during one fluorescence exposure period based on radiation of excitation light. Thereby, one image picked up by the CMOS sensor 23b is read non-destructively twice.

Furthermore, in the present embodiment, the image pickup device driver 48 sets gains at reading of one picked-up image performed twice to the gains $\alpha 1$ and $\alpha 2$ which are mutually different. For example, at the first reading, the gain of the amplification section A constituting each pixel of the CMOS sensor 23b is set to $\alpha 1$. Thereby, voltage based on signal charge of each pixel is amplified by the gain $\alpha 1$ and is supplied from the switch S to the ADC 71 via the column line CA and the CDS circuit 70. In this way, each pixel signal is amplified by the analog gain $\alpha 1$ before A/D conversion.

At the second reading, the image pickup device driver 48 sets the gain of the amplification section A constituting each pixel of the CMOS sensor 23b to $\alpha 2$. Thereby, the voltage based on signal charge of each pixel is amplified by the gain $\alpha 2$ and is supplied from the switch S to the ADC 71 via the column line CA and the CDS circuit 70. That is, at the second reading, each pixel signal is amplified by the analog gain $\alpha 2$ before A/D conversion.

In FIG. 9(a), a period shown being filled indicates a reset period, and a fluorescence exposure period is indicated by a frame next to the reset period. As shown in FIGS. 9(a) and 9(b), reading of two frames is performed for one fluorescence exposure period. Note that exposure and reading are controlled for each line, and exposure and reading of each pixel are not performed during all of the exposure periods and transfer/reading periods in FIGS. 9(a) and 9(b).

In this way, a picked-up image corresponding to FIG. 5(c) is obtained by the first reading of the two-time non-destructive readings, and a picked-up image corresponding to FIG. 5(d) is obtained by the second reading. An image pickup signal by the first reading of the two-time non-destructive readings is provided to the synchronization memory 45a via the color balance adjustment circuit 43 and the selector 44. An image pickup signal by the second reading is provided to the synchronization memory 45b via the color balance adjustment circuit 43 and the selector 44.

The image processing circuit 46 determines an arithmetic mean of images stored in the synchronization memories 45a and 45b. In this way, an image corresponding to FIG. 5(e) is obtained. The image processing circuit 46 assigns a fluorescence image obtained by determining the arithmetic mean, to first to third color channels to output the image to the DACs 47a, 47b and 47c. The DACs 47a, 47b and 47c convert the inputted signal to an analog signal and output the signal to the monitor 5. In this way, the fluorescence image is displayed on the monitor 5.

Figure 10:
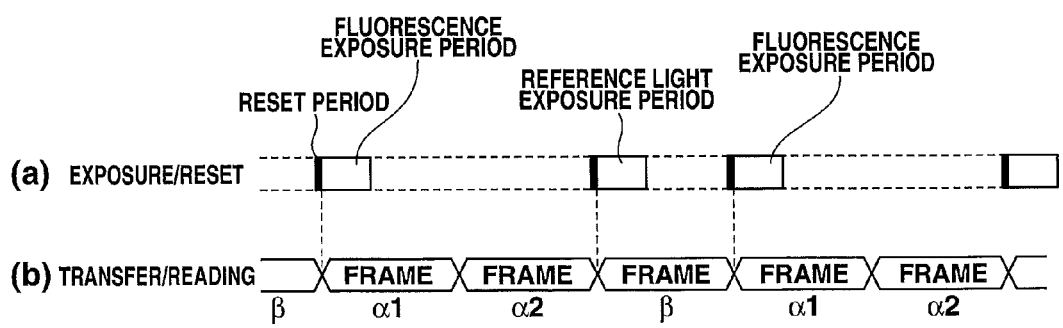
FIG. 10 is a timing chart for illustrating an operation of the present embodiment.

If the fluorescence observation mode for causing the excitation light LED 31b and the reference light LED 31c to alternately emit light is specified by a mode switching control signal, illumination and exposure is performed at timings shown in FIG. 10. That is, as shown in FIGS. 10(a) and 10(b), reading of two frames is performed for one fluorescence exposure period, and reading of one frame is performed for one reference light exposure period.

The image pickup device driver 48 switches analog gain between $\alpha 1$ and $\alpha 2$ at the time of performing two-time non-destructive readings corresponding to one-time fluorescence exposure, and sets the analog gain to $\beta$ at the time of performing one-time reading corresponding to one-time reference light exposure. Because the amount of reference light is sufficiently large in comparison with fluorescence, $\beta<\alpha1<\alpha2$ is set.

In this way, picked-up images corresponding to FIGS. 5(c) and 5(d) are obtained by two-time non-destructive readings corresponding to fluorescence exposure, and a reference light image is obtained by one-time reading corresponding to reference light exposure. The images are provided to the synchronization memories 45a to 45c, respectively, via the white balance adjustment circuit 43 and the selector 44. For example, signals based on the two-time readings corresponding to fluorescence exposure are stored in the synchronization memories 45a and 45b, respectively, and a signal corresponding to reference light exposure is stored in the synchronization memory 45c.

The image processing circuit 46 determines an arithmetic mean of the images stored in the synchronization memories 45a and 45b. Furthermore, by assigning a fluorescence image obtained by determining the arithmetic mean and a reference light image read from the synchronization memory 45c to the first to third color channels to output the images to the DACs 47a, 47b and 47c, the image processing circuit 46 performs image integration so that the fluorescence image and the reference light image are included in the same observed image. The DACs 47a, 47b and 47c convert the inputted signals to analog signals and output the signals to the monitor 5. In this way, the observed image in which the reference image and the fluorescence image are integrated is displayed on the monitor 5.

As described above, in the present embodiment, processing of reading signal charge accumulated in the CMOS sensor non-destructively twice without performing reset is performed. In this case, at the first reading, as for analog gain at a pre-stage of the column ADC, input voltage is multiplied by $\alpha1$ times the gain and, after that, A/D conversion is performed to send a signal to the processor. At the second reading, input voltage is multiplied by $\alpha2$ times the gain at the pre-stage of the column ADC to perform similar processing. In the present embodiment, two images with different brightnesses can be obtained by multiplication by different gains, such as $\alpha1<\alpha2$, at the time of first and second non-destructive readings. The processor is provided with frame memories for storing two images, and a fluorescence image is obtained by determining an arithmetic mean of the two images with different brightnesses. Unlike amplification processing performed inside the processor, signal level adjustment is performed for a voltage signal before being converted to tones by A/D conversion. Therefore, even in the case of performing amplification of an extremely dark fluorescent area with a relatively large gain value $\alpha2$, it is possible to improve visibility while preventing tone omission and whitishness.

(Modification)

Figure 11:
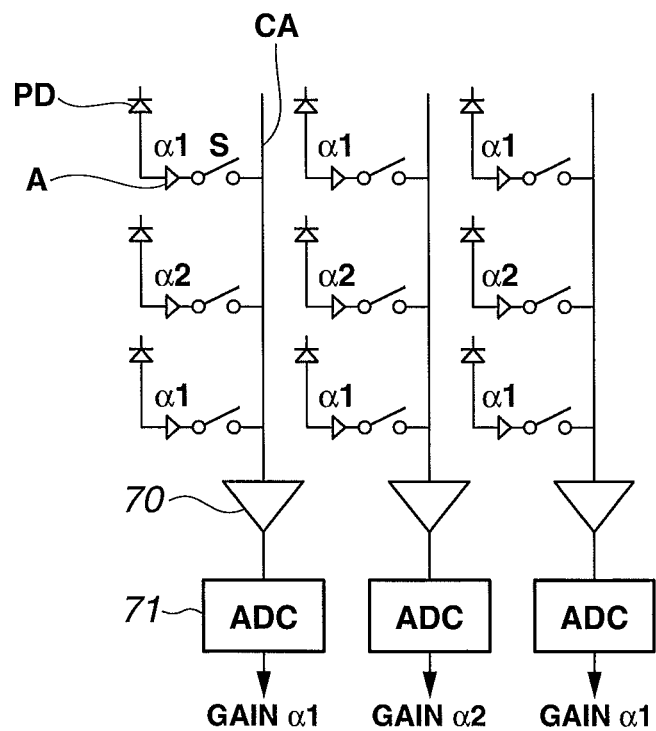
FIG. 11 is a diagram for illustrating a modification.

FIG. 11 is a diagram for illustrating a modification. In FIG. 11, the same things as in FIG. 8 are given the same reference numerals, and description thereof will be omitted.

In the above description, two picked-up images with different brightnesses are obtained for the same image by changing analog gain at the time of performing non-destructive reading twice. In comparison, FIG. 11 shows an example in which the gain of the amplification section A is switched for each line. For example, the gain of the amplifications A of odd lines is set to $\alpha1$, and the gain of the amplifications A of even lines is set to $\alpha2$.

Thereby, an image obtained by all pixels of odd lines of one fluorescence image is amplified by analog gain of $\alpha1$, and an image obtained by all pixels of even lines is amplified by analog gain of $\alpha2$. Therefore, by performing reading once, two images with different brightnesses can be obtained from one picked-up image.

Note that the two images have either information about the even lines or information about the odd lines, respectively, and two images having pixel values of all the lines can be generated by interpolation processing. By determining an arithmetic mean of the two images with different brightnesses obtained in this way, by a processor, it is possible to obtain a fluorescence image with improved visibility while preventing tone omission and whitishness.

Thus, in the present modification also, it is possible to obtain effects similar to those in the case of switching analog gain for each screen. That is, as for at least one of the two images with different amplification factors, bright fluorescent areas, dark fluorescent areas and parts other than fluorescent areas can be obtained in a state that appropriate tone values are maintained without occurrence of halation or blackishness, and, therefore, it is possible to, by determining a arithmetic mean of both images, perform observation under appropriate brightness and tone expression even in the case where multiple fluorescent areas with a large brightness/darkness difference exist. Furthermore, since the arithmetic mean is determined by reading the same optical image twice by non-destructive reading of the CMOS sensor, it is possible to avoid image position displacement which easily occurs at the time of operating an endoscope. Furthermore, the present modification has an advantage of capable of reading during one frame period and increasing frame rate.

In the above embodiment, an example of performing reading non-destructively twice for one-time fluorescence exposure has been described. However, it is also possible to perform reading three or more times, while changing analog gain, and obtain a fluorescence image by determining an arithmetic mean of three or more images.

In the above embodiment, an example of changing analog gain by each screen or each line has been described. It is, however, apparent that the analog gain may be changed by each predetermined range of pixels.

What is claimed is:

1. A medical instrument comprising:
   an illumination section radiating excitation light for exciting a fluorescent substance given to a subject, to the subject;
   an image pickup section photoelectrically converting reflected light from the subject to which the excitation light is radiated, to pick up an image of the subject;
   a reading section holding pixel signals obtained by the photoelectrical conversion and capable of reading the pixel signals non-destructively while changing amplification factors of the held pixel signals by a predetermined unit of pixels; and
   an image processing section determining an arithmetic mean of the pixel signals read with different amplification factors by the reading section to generate an image.

2. The medical instrument according to claim 1, wherein the reading section performs non-destructive reading multiple times, changing an amplification factor for each screen of the image pickup section.

3. The medical instrument according to claim 2, wherein the reading section performs non-destructive reading twice with a first amplification factor corresponding to a brightness of an area with brightness higher than a first brightness in an image configured by pixel signals obtained by the image pickup section and a section amplification factor, greater than the first amplification factor, corresponding to a brightness of an area with a brightness equal to or lower than a second brightness in the image.

4. The medical instrument according to claim 1, wherein the reading section performs reading once, changing an amplification factor for each reading line of the image pickup section.

5. The medical instrument according to claim 4, wherein the reading section performs reading once with a first amplification factor corresponding to a brightness of an area with brightness higher than a first brightness in am image configured by pixel signals obtained by the image pickup section and a second amplification factor, greater than the first amplification factor, corresponding to a brightness of an area with a brightness equal to or lower than a second brightness in the image.

6. The medical instrument according to claim 5, wherein the image processing section interpolates each of pixel signals read with the first and second amplification factors to configure an image of one screen respectively and determines an arithmetic mean of the images of the configured two screens to generate an image.

7. The medical instrument according to claim 1, comprising
a conversion section converting the pixel signals read by the reading section to digital signals.

8. The medical instrument according to claim 1, wherein
the illumination section radiates reference light time-sequentially in addition to the excitation light;
the image pickup section performs image pickup based on reflected light of the reference light in addition to the reflected light based on the excitation light; and
the reading section performs reading of a pixel signal based on the reference light at an amplification factor lower than an amplification factor for reading of a pixel signal based on the excitation light.

9. The medical instrument according to claim 8, wherein
the reading section performs non-destructive reading twice for the pixel signal based on the excitation light during a period of radiation of the excitation light, while changing an amplification factor for each screen, and performs reading once for a pixel signal based on the reference light during a period of radiation of the reference light.

* * * * *

UNITED STATES PATENT AND TRADEMARK OFFICE
CERTIFICATE OF CORRECTION

PATENT NO. : 8,545,399 B2
APPLICATION NO. : 13/715138
DATED : October 1, 2013
INVENTOR(S) : Shunji Takei et al.

It is certified that error appears in the above-identified patent and that said Letters Patent is hereby corrected as shown below:

Title Page, Item 72

It Should Read:

Inventors: Shunji Takei, Hachioji (JP); Wataru Ono, Hachioji (JP)

Signed and Sealed this
Fourth Day of February, 2014

Michelle K. Lee
*Deputy Director of the United States Patent and Trademark Office*